United States Patent [19]

Petrow

[11] Patent Number: 4,841,997

[45] Date of Patent: Jun. 27, 1989

[54] METHOD FOR SETTING HAIR OR FUR

[76] Inventor: Henry G. Petrow, 32 Garfield St., Watertown, Mass. 02172

[21] Appl. No.: 142,115

[22] Filed: Jan. 7, 1988

[51] Int. Cl.$^4$ .............................................. A45D 7/00
[52] U.S. Cl. ..................................... 132/204; 424/71
[58] Field of Search ....................... 132/204, 205, 210; 424/70, 71, 72

[56] References Cited

U.S. PATENT DOCUMENTS

| | | | |
|---|---|---|---|
| 4,134,411 | 1/1979 | Yamazaki | 132/205 |
| 4,273,143 | 6/1981 | Klemm et al. | 132/204 |
| 4,296,764 | 10/1981 | Pallone et al. | 132/204 |
| 4,322,401 | 3/1982 | Harada | 424/72 |
| 4,373,540 | 2/1983 | de la Guardia | 132/204 |
| 4,423,032 | 12/1983 | Abe et al. | 424/70 |
| 4,426,376 | 1/1984 | Shirakura et al. | 424/71 |
| 4,465,664 | 8/1984 | Matsunaga et al. | 424/71 |
| 4,504,466 | 3/1985 | Eda | 424/72 |
| 4,547,365 | 10/1985 | Kubo et al. | 424/71 |
| 4,548,811 | 10/1985 | Kubo et al. | 424/71 |
| 4,560,554 | 12/1985 | Kubo et al. | 424/71 |
| 4,659,566 | 4/1987 | Petrow | 424/71 |

FOREIGN PATENT DOCUMENTS

| | | |
|---|---|---|
| 0167866 | 1/1986 | European Pat. Off. . |
| 0235783 | 9/1987 | European Pat. Off. . |
| 29234 | 3/1976 | Japan . |

*Primary Examiner*—Robert Peshock
*Assistant Examiner*—J. Hakomaki
*Attorney, Agent, or Firm*—Panitch Schwarze Jacobs and Nadel

[57] ABSTRACT

A method of setting hair or fur comprises applying to the hair or fur a composition for reducing keratin disulfide bonds, allowing the hair or fur to stand in a desired configuration, applying to the hair or fur a composition to set the hair or fur in a desired wave or straightened configuration, and washing or drying the hair or fur, where the composition to set the hair or fur is an ionic, water-soluble compound, which is substantially non-oxidizing to the products of keratin reduction and which reforms substantially all the keratin disulfide bonds, while substantially avoiding precipitation. The kit comprising and facilitating the same method is included.

25 Claims, No Drawings

METHOD FOR SETTING HAIR OR FUR

FIELD OF THE INVENTION

The present invention relates to a method of setting hair or fur, including a kit comprising the same and, more particularly, to a method of reforming substantially all the keratin disulfide bonds in hair or fur, while substantially avoiding precipitation.

BACKGROUND OF THE INVENTION

Permanent waving and straightening of hair are common techniques for beautifying hair or fur by permanently forming or setting the hair or fur into a desired configuration. Various techniques have been practiced for many years in the hair and fur industries, such as in hair salons, and in the home practiced by an individual.

Hair and fur is comprised of keratin, which is a polyamide cross-linked by disulfide bonds. The disulfide bonds are responsible for the hair or fur being maintained in a particular configuration. In a conventional hair waving or straightening process, the hair is first softened or relaxed by breaking the disulfide bonds in the keratin with a reducing agent and then hardening the hair or fur in the desired configuration by stopping the reduction reaction and restoring or reforming disulfide bonds by applying an oxidizing agent, generally referred to in the art as a neutralizer.

Dissolved salts and esters of thioglycolic acid and aqueous solutions of sulfites and/or bisulfites have gained wide acceptance as the preferred agents for reducing keratin disulfide bonds. The most common reducing agents in the professional market are the thioglycolates, including thioglycolate, dithioglycolate, thioglycolic acid and its ester, glyceryl monothioglycolate or GMT. Toni Silk Wave, a product of the Gillette Company, Boston, Mass. and Ogilvie Body and Styling Wave, a product of Ogilvie Products, Inc., Montvale N.J., are examples of thioglycolate systems known in the art. Toni Silk Wave contains 0.7N thioglycolic acid at pH 9.3; Ogilvie's Body and Styling Wave contains 1.0N thioglycolate and 0.4N dithioglycolate, and has a pH of 9.3.

The sulfite/bisulfite solutions are sometimes used by the professional market, but are more common for use at home by individuals because of their relatively gentle action and general absence of odor. Generally, sulfite solutions are comprised of ammonium sulfite and ammonium bisulfite in a molar ratio of about 1:1. Rave® Performance Perm is one example of an ammonium sulfite/bisulfite reduction system known in the art. Rave® is an ammonium sulfite/bisulfite mixture containing 1.5N sulfite and 12% to 14% urea, and having a pH of 7.3.

It is recognized by those skilled in the art that keratin disulfide bonds are represented as "KSSK", wherein K represents keratin moieties and SS represents the disulfide bond. The reaction of a sulfite with keratin causes the disulfide bonds to be split into two fragments, present in an essentially 1:1 stoichiometric ratio—reduction to a mercaptan or thiol (KSH) and oxidation to a thiosulfate ($KSSO_3^-$) commonly called a Bunte salt —as indicated in the following equation:

$$KSSK + HSO_3^- \rightarrow KSH + KSSO_3^- \qquad (I)$$

Thioglycolic acid is a thiol, which generally exists as the anion, $OCCH_2SH$, at the pH values commonly used in practice. The reaction of thioglycolic acid with keratin differs from the sulfite reaction and results in several end products as noted below. Keratin reaction with thioglycolic acid may be represented as follows:

$$KSSK + 2RSH \rightarrow 2KSH + RSSR \qquad (II)$$

wherein RSH is thioglycolic acid and RSSR represents the disulfide of thioglycolate. The laws of chemical equilibrium demand that the actual products of this reaction also include, in variable stoichiometric amounts, KSSR, a hybrid disulfide of keratin and thioglycolate. Therefore, KSSK, KSSR, RSSR, RSH and KSH will be present in the hair or fur after treatment with thioglycolic acid. Thorough rinsing will remove much of the RSSR and RSH from the hair or fur. Any product containing KS— is essentially fixed within the hair or fur.

Several oxidizing or neutralizing agents are well known in the art, including aqueous hydrogen peroxide and aqueous sodium bromate. However, when sulfite systems are used to reduce the disulfide bonds, conventional oxidizing agents do not reverse the disulfide splitting reaction and only the thiol fragments are reformed to disulfide, as shown in Equation III:

$$2KSH + H_2O_2 \rightarrow KSSK + 2H_2O \qquad (III)$$

Bunte salt is very resistant to oxidation and does not react with oxidants to reform keratin disulfide bonds. Consequently, only one-half of the disulfide bonds reduced by sulfite systems are restored and the resulting hair or fur configuration is weak, of poor durability, and the overall tensile strength of the hair or fur is impaired.

When thioglycolate systems are used to reduce the keratin disulfide bonds in the hair or fur, the thiol fragments are restored to disulfide as in Equation III when reacted with an oxidizing agent. Those fragments existing as KSSR, however, cannot be reformed by an oxidative process. Moreover, the greater the quantity of KSSR formed, the lesser the holding strength of the desired configuration of the hair or fur, the weaker the tensile strength of the hair or fur, and the greater the hair or fur is open to damage.

A high percentage of KSSR resulting from the reduction of the disulfide bonds has long been a problem in the art. For example, if the thioglycolate concentration is too high, or if the reduction agent is permitted to react for too long a time, the fraction of keratin converted to KSSR can increase to an unacceptable level. This condition, when it occurs, is generally referred to as "overprocessing."

Attempts in the prior art to avoid the problems inherent with conventional neutralizers include use of simple and amino salts in conjunction with an organo-carbonate promoter as neutralizer in sulfite systems. See Japanese Patent Application No. 49-101743 of Okauchi. However, such systems cause sulfite precipitation—an undesirable reaction in hair care technology, which is substantially avoided in this invention.

In view of the serious deficiencies and inefficiencies of the prior art, it is desirable to neutralize hair relaxed or softened by either a thioglycolate or a sulfite in such a way so as to have reformation of substantially all the keratin disulfide bonds while substantially avoiding precipitation. A water soluble, safe, non-toxic neutralizer is desirable.

BRIEF SUMMARY OF THE INVENTION

According to the present invention, in a method for setting hair or fur, comprising applying to the hair or fur a composition for reducing keratin disulfide bonds, allowing the hair or fur to stand in the desired configuration, applying to hair or fur a composition to set the hair in a desired wave or straightened configuration, and washing or drying the hair or fur, the composition to set the hair or fur is an ionic, water soluble compound, which is substantially non-oxidizing to the products of keratin reduction and which reforms substantially all the keratin disulfide bonds, while substantially avoiding precipitation.

The setting composition is preferably an aqueous solution of a polyvalent electrolyte selected from the group consisting of sodium sulfate, ammonium sulfate, calcium chloride, magnesium sulfate, magnesium chloride, lanthanum chloride, lanthanum sulfate and potassium aluminum sulfate, a form of aluminum alum.

In addition, the present invention further comprises a kit for setting hair or fur in a desired waved or straightened configuration, comprising a composition for reducing keratin disulfide bonds and an ionic, water soluble compound for reforming substantially all the keratin disulfide bonds, which is substantially non-oxidizing to the products of keratin reduction and which substantially avoids precipitation. The reducing composition is preferably selected from the group consisting of a soluble sulfite, bisulfite, thioglycolate and thioglycolic acid. The reforming compound is preferably selected from the setting composition group described above.

DETAILED DESCRIPTION OF PREFERRED EMBODIMENTS

Although the method of the present invention applies to the setting of hair or fur generally, the method is described and exemplified below with specific examples using human hair and magnesium sulfate. It will be understood by one skilled in the art that magnesium sulfate is merely illustrative of the surprising and effective methods of the present invention. Magnesium sulfate is desirable for exemplificaton purposes because it is relatively safe to handle, non-toxic, and inexpensive. In addition, one skilled in the art will recognize that other hair or fur is believed to be similarly treatable by this invention.

In the present invention, keratin disulfide bonds are reduced using a reducing compound such as the Rave®, Toni and Ogilvie products described above. It will be apparent to one skilled in the art, however, that other, analogous reducing compounds may be used to reduce keratin disulfide bonds in hair or fur for subsequent treatment in accordance with the present invention.

Following reduction in a manner recommended by the manufacturer of the particular reducing compound employed, the hair or fur is washed or rinsed. Where thioglycolate systems are used to reduce the disulfide bonds, it is desirable to rinse hair or fur after reduction treatment to reduce side reactions with the thiols in the reduction compound and to reduce cross-linking interferences. Where sulfite systems are employed to reduce the disulfide bonds, it is similarly desirable to rinse hair or fur to reduce the exothermic nature of the neutralization process.

Conventional rinsing is typically comprised of washing with running water for several minutes. In the present invention, it is preferred that the hair or fur be rinsed with an ionic neutralizing solution (discussed below) in addition to water. It has been found that the valency of the ionic species strongly affects the preferred concentration range with increased valency of cationic species producing a more pronounced improvement than increased valency of anionic species.

According to the present invention, after reduction of the disulfide bonds and rinsing of the hair or fur, a neutralizing or setting composition is applied to set the hair or fur in a desired waved or straightened configuration. The desired configuration is generally established by methods and devices known in the art, such as curlers, crimping devices and straightening devices, among others. Such straightening or curling methods and devices may be employed before and/or during application of the setting composition, as may be desired by the individual practicing the methods of this invention.

The setting composition according to the present invention is preferably an ionic, water soluble compound, which reforms substantially all the keratin disulfide bonds, which is substantially non-oxidizing to the products of keratin reduction and which substantially avoids precipitation. An aqueous solution of an electrolyte, such as a 3N sodium chloride, potassium chloride, ammonium chloride solution or a mixture thereof is suitable. However, other, analogous electrolytic solutions may be substituted. Particularly preferable is an aqueous solution of polyvalent electrolyte. Examples of such polyvalent electrolytes include sodium sulfate, ammonium sulfate, calcium chloride, magnesium sulfate, magnesium chloride, lanthanum chloride, lanthanum sulfate, potassium aluminum disulfate and mixtures thereof. Other, analogous polyvalent electrolytes may be used as setting compositions in accordance with the present invention, as will be appreciated by one skilled in the art.

It is desirable in the present invention to substantially avoid precipitation, which may occur using conventional setting compositions, particularly those used in conjunction with sulfite reduction systems. The various sodium, potassium and ammonium salts of the present invention are not sulfite precipitators. Magnesium ion does not precipitate sulfite, even when added to the undiluted sulfite lotion (unrinsed hair). While lanthanum and calcium sulfite are fairly insoluble, their bisulfites, the ion produced by the reversal of Equation I, are soluble at the optimum concentrations discussed below. A setting composition according to the present invention substantially avoids precipitation and the problems associated therewith, such as removing the operating ion (e.g.: Ca, Mg, La, etc.) from solution as well as depositing undesirable solids within the hair or fur, among other problems.

The preferred concentration range of each electrolyte in solution varies with the particular electrolyte employed. It has been found that the following respective concentrations in aqueous solution are generally preferable for use in accordance with the present invention: sodium sulfate—about 1.8N to about 3.0N; ammonium sulfate—about 1.9N to about 2.8N; calcium chloride—about 0.5–0.9N; magnesium chloride—about 0.2N to about 1.2N; magnesium sulfate—about 0.1N to about 0.9N; lanthanum chloride—about 0.07 to about 0.4N; lanthanum sulfate—about 0.03 to about 0.2N and potassium aluminum sulfate—about 0.1N to about 0.4N.

Where GMT is employed as the reducing agent, the following respective concentrations are particularly preferable: lanthanum chloride—about 0.5N to about 1.0N; magnesium sulfate—about 1.5N to about 3.0N; and potassium aluminum sulfate—about 1.0N.

The setting compositions according to the present invention may be applied to hair or fur preferably for a time period of about three minutes to about ten minutes. The particular time the setting composition is to be applied to the hair or fur may be determined by one skilled in the art, based upon such factors as the type or consistency of hair or fur, the temperature of the hair/solution environment and other factors. For example, it is known in the art that bleached hair or fur is more porous and, therefore, more reactive to permanent waving and straightening than is normal or unbleached hair or fur. It may be sufficient, then, to apply the setting composition of the present invention for a relatively short period of time.

Unlike oxidizing agents, such as hydrogen peroxide or sodium bromate, the setting agents of this reaction are unreactive towards hair and there are no harmful effects associated with their use. Thus, they may be applied to hair or fur for periods beyond the time needed to function effectively, without appreciable risk to the health of the hair. Such is not the case when employing an oxidant as the neutralizer.

The neutralizing solutions of the present invention may be applied in the presence of various additives known in the art, such as wetting agents or surfactants (e.g.: sodium lauryl sulfonate), conditioning agents (e.g.: ammonium salts), emollients (e.g.: mineral oil), and the like. Such additives are believed to have no effect on the neutralization process of the present invention. While such additives may be desirable, they are not essential for the present invention.

In one preferred embodiment, the setting compositions of the present invention are simply washed or rinsed from the hair or fur upon the expiration of the neutralizing time period described above without further treatment. In another preferred embodiment, it is desirable, preferably when used in conjunction with thioglycolate reduction systems, to apply the setting composition in the presence of or prior to application of an oxidant. It is believed, while not wishing to be bound by any particular theory, that when hair or fur is processed by thioglycolate systems, any KSSR formed cannot participate as does KSH in the reaction of Equation III, leaving uncrosslinked (i.e., non-KSSK) disulfide species in the hair or fur.

An oxidant will reform the keratin disulfide bonds with KSH, as shown in Equation III. Examples of such oxidants include bromates, perborates, peroxides and persulfates. It will be appreciated by one skilled in the art, however, that other, analogous oxidants may be used in conjunction with or subsequent to application of the setting composition of the present invention. Oxidants applied in the manner described above are available commercially, and may be employed in concentrations (typically an about 2% to about 10% by weight aqueous solution) and for periods of time supplied and recommended by the manufacturer.

It may be desirable to apply heat to the hair or fur during the practice of the present invention, particularly during conventional reduction of the disulfide bonds. It is believed that heat applied during the setting process of this invention has no adverse effect on the quality of the resulting waved or straightened configurations. Although heat is not critical to the setting process, the reactions involved may be accelerated by such heating.

It is known in the art that heat may be applied to hair or fur by loosely wrapping the hair or fur in plastic sheeting and applying a source of heated air, such as a conventional hair dryer. It will be appreciated by one skilled in the art that other, analogous methods of heat application, such as heated rollers, may be used in conjunction with this invention. The time period and temperature (typically 10–20 minutes at 110°–130° F.) of the applied heat may be determined by one skilled in the art.

The practice of the present invention may be facilitated by a kit including reducing compounds, setting compositions and optional oxidants, all as described above. Such a kit may be individually designed to include methods and compositions for a desired reduction system. Moreover, such a kit may be designed for use in the professional market or for use in the home. One skilled in the art may determine the desired composition of a kit including the methods and compositions of the present invention.

While the inventor does not wish to be bound by any particular theory, it is believed that because the salt solutions of the setting compositions of the present invention are substantially without oxidizing power, a Donnan ion exclusion process is involved whereby sulfite and/or bisulfite ions are expelled from the keratin, thereby allowing the reversal of Equation I, above, through transfer of sulfite ions from the keratin phase into the external, aqueous phase.

In thioglycolate systems, especially those with relatively higher thioglycolate (and its derivatives) concentrations, such as the Ogilvie lotion described above, it is believed, while not wishing to be bound by any particular theory, that prior to neutralization, reduced keratin hair would have a greater fraction of broken disulfide bonds as KSSR and that utilizing the ion exclusion mechanism described above, the following bond reforming action would result in enhanced neutralization:

$$KSH + KSSR \rightarrow KSSK + RSH \qquad (IV)$$

$$2KSSR \rightarrow KSSK + RSSR \qquad (V)$$

The reaction is driven to completion by the Donnan exclusion of the ionic $RSH(HSCH_2COO^-)$ and $RSSR\ [(HSCH_2COO^-)_2]^=$. Therefore, for example, if 40% of the split disulfide bonds exist as KSSR, ion exclusion would lead to 80% bond reformation, whereas the use of an oxidant, ineffective with KSSR, would reform only 60% of the disulfide bonds.

Where GMT is employed to reduce the disulfide bonds, it is believed, although the inventor does not wish to be bound by any particular theory, that a higher concentration of the ionic setting solution is preferable to overcome the non-ionic nature of GMT.

The invention will now be illustrated in further detail by reference to the following specific, non-limiting examples.

Several types of hair were used to demonstrate the effectiveness of the setting composition of the present invention. As will be appreciated by one skilled in the art, hair or fur having different characteristics, such as color, source and condition, among others, accepts permanent waving or straightening techniques with varying degrees of efficiency. The hair samples used in the following examples were 8-inch, 0.5 gram tresses, clipped or tied off at one end, of dark brown Caucasian hair. Other samples included tresses of dark brown Caucasian hair bleached to medium brown and light brown. Also, naturally curly Caucasian hair tresses were used for examples of hair straightening.

Sulfite Systems

EXAMPLE 1

Hair tresses of dark brown Caucasian hair were prepared for curling. The tresses were shampooed and thoroughly rinsed. After the tresses had been rolled on a 5/16" curling rod, they were saturated with the Rave ® reducing lotion, loosely wrapped in plastic and heated to about 90° Fahrenheit for the time period of about 45 minutes, recommended by the manufacturer. After the reaction, the samples were washed for three minutes in running water.

One set of tresses was neutralized in a conventional manner by applying 2% by weight hydrogen peroxide for five minutes. A series of similar tresses was neutralized for five minutes with 3N sodium chloride (16% by weight) solutions containing one each of 2%, 1%, 0.5%, 0.25% and 0% by weight hydrogen peroxide, followed by rinsing for three minutes with water, while still on the rods.

The various curled products were then compared for curl formation, spring, and durability after multiple shampooings, using subjective tests accepted as standard and informative by those skilled in the art.

It was found that as the quantity of hydrogen peroxide in the neutralizing solution was reduced, the curl obtained was tighter, more springy, more durable, and lost increasingly less strength after many shampooings. Moreover, it was found that a neutralizing solution of about 2.6N to about 3.0N sodium chloride with no hydrogen peroxide yielded the most desirable curls. Sodium chloride concentrations as low as about 1N and as high as about 5N were found to work and produce a permanent wave condition, albeit inferior to the condition resulting when the preferred concentration range of sodium chloride was employed.

Similar results were found using ammonium chlride, potassium chloride, sodium nitrate, potassium iodide, and sodium bromide neutralizers having solution concentrations in the range of about 2.6N to about 3.0N and no hydrogen peroxide. Neutralizing times of about three minutes to about ten minutes were employed with all neutralizers and found not to exhibit significantly different results at temperatures comparable to human body temperature. At 65° Fahrenheit, however, a neutralizing time of ten minutes yielded better results than one, of three minutes.

EXAMPLE 2

Hair tresses similar to those used in Example 1 were prepared, reduced and washed in the manner of Example 1. The following series of polyvalent electrolytes were used separately as neutralizing compositions: sodium sulfate, ammonium sulfate, calcium chloride, magnesium chloride, magnesium sulfate, lanthanum chloride, lanthanum sulfate and potassium aluminum sulfate. Each composition was applied using the same neutralizing procedures described for the sodium chloride solution in Example 1. The resulting waved conditions are presented in Table 1 with the concentration expressed in normality and percent by weight for each electrolyte, as well as comparative results for one-third of and two times the preferred concentration.

TABLE 1

| Salt | Preferred Concen. N | Preferred Concen. % | Curl Formation Preferred Concen. | ⅓ Pref. | 2× Pref. |
|---|---|---|---|---|---|
| Na$_2$SO$_4$ | 1.8 | 14 | Excellent | Poor | Fair (Saturated 3N Solution) |
| (NH$_4$)$_2$SO$_4$ | 1.9 | 12 | Excellent | Poor | Fair |
| CaCl$_2$ | 0.8 | 4.3 | Excellent | Fair | Fair |
| MgCl$_2$ | 0.6 | 2.8 | Excellent | Fair | Fair |
| MgSO$_4$ | 0.3 | 1.7 | Excellent | Fair to Good | Good |
| LaCl$_3$ | 0.2 | 1.6 | Excellent | Fair | Fair |
| La$_2$(SO$_4$)$_3$ | 0.08 | 0.8 | Excellent | Fair | Fair |
| KAl(SO$_4$)$_2$ | 0.2 | 1.3 | Excellent | Fair | Good |

Table 1 shows that the concentration of the polyvalent salt required to achieve excellent stable curls in conjunction with reducing systems other than GMT is greatly lower than the concentration of the monovalent electrolyte, sodium chloride, used in Example 1. In addition, these salts, surprisingly, yielded stronger, more durable curls than did any of the monovalent electrolytes. The curls obtained using the polyvalent electrolytes were vastly superior to those obtained when using hydrogen peroxide, as practiced in the prior art. Neutralization times of about three minutes to about ten minutes were employed, and no significantly different results were noted.

EXAMPLE 3

To determine whether and how bleached hair affected the efficacy of the neutralizing composition of the present invention, strongly bleached, highly porous hair was prepared, and then treated and washed in the manner described in Example 1. When neutralized in the manner described in Example 1 using 0.6N magnesium sulfate, the resulting curl was strong and durable, and differed minimally from the curl obtained using the same process on unbleached hair. Using 2% hydrogen peroxide as the neutralizer, however, the strongly bleached hair yielded almost no curl.

EXAMPLE 4

To determine whether the relatively high concentration of urea in Rave ® any effect on the neutralizing ability of the mono- and polyvalent electrolytes listed above, a lotion containing only ammonium sulfite and ammonium bisulfite in an about 1:1 molar ratio, equivalent to that found in Rave ®, was prepared and applied to tresses as described in Example 1. No effect upon the neutralizing properties of magnesium sulfate, lanthanum sulfate, and sodium sulfate was observed.

Thioglycolate Systems

EXAMPLE 5

The Toni lotion, described above, was applied in the manner and for the period of time (about 20 minutes) recommended by the manufacturer to hair tresses similar to and prepared in the same manner as described in Example 1. After the reaction, the tresses were washed for three minutes in running water. A 0.3N magnesium sulfate solution, applied for five minutes before rinsing with water, was used as the neutralizing agent for certain tresses. For comparison purposes, the hydrogen peroxide neutralizer furnished with the Toni products was applied as directed by the manufacturer as the neutralizing agent for other, similar tresses.

The magnesium sulfate neutralizer yielded a stronger, better formed and more durable curl than did the curl resulting from the hydrogen peroxide neutralizer.

EXAMPLE 6

After preparation and treatment of tresses as described in Example 5, 0.3N magnesium sulfate solution was applied as described in Example 5, rinsed with water for about one minute and then followed by an application of a 2% by weight hydrogen peroxide solution for about two minutes.

It was found that a tighter, stronger and more durable curl resulted from this two-step neutralization treatment than the curls resulting from magnesium sulfate alone. Both the magnesium sulfate application of Example 5 and the magnesium sulfate followed by hydrogen peroxide performed in this example yielded superior curls to those yielded in Example 5 by the hydrogen peroxide neutralizer alone.

The two-step neutralization process (i.e., magnesium sulfate followed by rinsing followed by hydrogen peroxide) was combined into a single step by applying the 0.3N magnesium sulfate solution in the presence of a 0.6N (1% by weight) hydrogen peroxide solution—a substantially lower concentration of hydrogen peroxide than is presently practiced in the art. The results were substantially similar to those following the two step neutralization process. Substitution of the 0.6N hydrogen peroxide with 1.0N sodium bromate (2.5% by weight solution) yielded an equivalent result.

Both the magnesium sulfate/hydrogen peroxide and magnesium sulfate/sodium bromate solutions yielded curls as durable, strong, and springy as the curls yielded in the two-step neutralization described above in this Example. It was found that hydrogen peroxide solutions with concentrations higher than 1N were somewhat less effective. Sodium bromate solutions with concentrations higher than about 2.0N were also found to be less effective than the 1.0N sodium bromate solution. However, when these solutions were left on for ten minutes, the higher concentrations of bromate and hydrogen peroxide were fully effective.

EXAMPLE 7

The reducing agent produced by Ogilvie, described above, was applied following the manufacturer's instructions to tresses, which were prepared as in Example 1. After washing for three minutes, certain tresses were treated with a 0.3N magnesium sulfate solution while other tresses were treated with the hydrogen peroxide neutralizer furnished with the Ogilvie product. After rinsing the magnesium sulfate solution with water for about one minute, one hair tress was then treated with a 2% by weight hydrogen peroxide solution.

The curls resulting after treatment with magnesium sulfate only and magnesium sulfate followed by hydrogen peroxide were both superior to the curl resulting after treatment with hydrogen peroxide alone. In addition, the curls resulting after application of magnesium sulfate or magnesium sulfate followed by hydrogen peroxide were of a substantially equivalent quality.

EXAMPLE 8

Tresses prepared as in Example 1 were overprocessed by receiving two treatments with the Ogilvie waving lotion with a water rinse in between treatments. One tress was neutralized with 3N hydrogen peroxide and a second tress was neutralized with 0.3N magnesium sulfate followed by a hydrogen peroxide solution. The tress that received only the peroxide treatment had a very limp and weak curl. The tress treated with the two-step neutralization of magnesium sulfate and hydrogen peroxide had a very tight, springy curl.

EXAMPLE 9

Three permanent waves were given at a professional salon, performed by a licensed beautician using the methods of this invention and other, conventional techniques. For two of the clients, Rave's ® Performance Perm was used as the waving lotion and an about 0.3N magnesium sulfate solution was employed as the neutralizer. For the third client, Ogilvie Body and Styling Wave was used as the reducing lotion and about 0.3N magnesium sulfate solution was employed as the neutralizer. All three clients received a strong, durable perm, having excellent spring, luster and body.

EXAMPLE 10

Hair tresses prepared as in Example 1 were treated with a reducing compound containing about 1.2N GMT (20% by weight solution) having an ammonia-adjusted pH of about 8. The GMT solution was freshly prepared to avoid hydrolysis and loss of efficiency. The GMT solution was applied for about 20 minutes with heating to about 98.6° Fahrenheit. After rinsing with water for three minutes, the tresses were individually neutralized for five minutes with: 2% aqueous hydrogen peroxide solution; 0.7N lanthanum chloride; 1.0N potassium aluminum sulfate; and 2.0N magnesium sulfate, respectively. The tresses were then rinsed for one minute with water.

It was found that the lanthanum chloride solution yielded curls better or equivalent to those formed by the potassium aluminum sulfate solution; both solutions yielded results better than the magnesium sulfate solution; and all three polyvalent electrolyte solutions yielded results superior to the hydrogen peroxide solution.

The procedures employed in the experiments above may also be applied for the straightening of hair. The difference between curling and straightening is a matter of the configuration chosen to hold the hair during treatment of reduction and reformation of the keratin disulfide bonds.

The present invention may be embodied in other specific forms without departing from the spirit or central attributes thereof and, accordingly, reference should be made to the appended claims, rather than the specification, as indicating the scope of the invention.

I claim:

1. In a method for setting hair or fur, comprising applying to the hair or fur a composition for reducing keratin disulfide bonds, allowing the hair or fur to stand in a desired configuration, applying to the hair or fur a composition to set the hair in a desired waved or straightened configuration, and washing and drying the hair or fur, the improvement comprising:

the composition to set the hair or fur being an ionic, water soluble compound, which is substantially non-oxidizing to the products of keratin reduction and which causes substantially all of the keratin disulfide bonds to reform while substantially avoiding precipitation.

2. The method according to claim 1, wherein the setting composition comprises an aqueous solution of a polyvalent electrolyte.

3. The method according to claim 2, wherein the polyvalent electrolyte is selected from the group consisting of sodium sulfate, ammonium sulfate, calcium chloride, magnesium sulfate, magnesium chloride, lanthanum chloride, lanthanum sulfate, and potassium aluminum sulfate.

4. The method according to claim 2, wherein the polyvalent electrolyte is sodium sulfate, and the concentration of the aqueous solution is about 1.8N to about 3.0N.

5. The method according to claim 2, wherein the polyvalent electrolyte is ammonium sulfate, and the concentration of the aqueous solution is about 1.9N to about 2.8N.

6. The method according to claim 2, wherein the polyvalent electrolyte is calcium chloride, and the aqueous solution is about 0.5N to about 0.9N.

7. The method according to claim 2, wherein the polyvalent electrolyte is magnesium chloride, and the concentration of the aqueous solution is about 0.2N to about 1.2N.

8. The method according to claim 2, wherein the polyvalent electrolyte is magnesium sulfate, and the concentration of the aqueous solution is about 0.1N to about 0.9N.

9. The method according to claim 2, wherein the polyvalent electrolyte is lanthanum chloride, and the concentration of the aqueous solution is about 0.07N to about 0.4N.

10. The method according to claim 2, wherein the polyvalent electrolyte is lanthanum sulfate, and the concentration of the aqueous solution is about 0.03N to about 0.2N.

11. The method according to claim 2, wherein the polyvalent electrolyte is potassium aluminum sulfate, and the concentration of the aqueous solution is about 0.1N to about 0.4N.

12. The method according to claim 1, wherein the setting composition is applied in the presence of heat.

13. The method according to claim 1, wherein the reducing agent is selected from the group consisting of sulfite, bisulfite, thioglycolate, dithioglycolate, thioglycolic acid and glyceryl monothioglycolic acid.

14. The method according to claim 13, wherein the reducing agent is glyceryl monothioglycolate and the setting composition is an aqueous solution selected from the group consisting of about 0.5N to about 1.0N lanthanum chloride, about 1.5N to about 3.0N magnesium sulfate and about 1.0N potassium aluminum sulfate.

15. The method according to claim 2, wherein the setting composition is about 0.3N magnesium sulfate and the reducing agent is ammonium sulfite/bisulfite solution having a molar ratio of about 1:1.

16. The method according to claim 1, wherein the setting composition is applied in the presence of an oxidant.

17. The method according to claim 16, wherein the oxidant is selected from the group consisting of bromates, perborates, peroxides and persulfates.

18. The method according to claim 16, wherein the setting composition is an aqueous solution of about 0.3N magnesium sulfate, the reducing agent is about 0.7N thioglycolic and the oxidant is an aqueous solution of about 0.6N hydrogen peroxide.

19. The method of claim 1, wherein the setting composition is selected from the group consisting of sodium chloride, potassium chloride and ammonium chloride.

20. A kit for setting hair or fur in a desired waved or straightened configuration, comprising:
a composition for reducing keratin disulfide bonds; and
an ionic, water soluble compound for reforming substantially all the keratin disulfide bonds, which is substantially non-oxidizing to the products of keratin production while substantially avoiding precipitation.

21. The kit according to claim 20, wherein the reducing composition is selected from the group consisting of sulfite, bisulfite, thioglycolate and thioglycolic acid.

22. The kit according to claim 20, wherein the reforming compound is selected from the group consisting of sodium sulfate, ammonium sulfate, calcium chloride, magnesium sulfate, magnesium chloride, lanthanum chloride, lanthanum sulfate, potassium aluminum sulfate, sodium 23. The kit according to claim 20, wherein the reducing agent is an ammonium sulfite/bisulfite solution having a molar ratio of about 1:1.

24. The kit according to claim 20, which further includes an oxidant.

25. The kit according to claim 24, wherein the reducing agent is about 0.7N thioglycolic acid, the reforming agent is an aqueous solution of about 0.3N magnesium sulfate and the oxidant is an aqueous solution of about 0.6N hydrogen peroxide.

* * * * *